US012723934B2

United States Patent
(12) Kim et al.

(10) Patent No.: US 12,723,934 B2
(45) Date of Patent: Sep. 1, 2026

(54) FIBER-BASED STRAIN SENSORS AND METHOD OF MANUFACTURING THE SAME

(71) Applicant: UIF (University Industry Foundation), Yonsei University, Seoul (KR)

(72) Inventors: Hyun Jae Kim, Seoul (KR); Tae Yoon Lee, Seoul (KR); Won Kyung Min, Seoul (KR); Chi Hyeong Won, Seoul (KR)

(73) Assignee: UIF (University Industry Foundation), Yonsei University, Seoul (KR)

( * ) Notice: Subject to any disclaimer, the term of this patent is extended or adjusted under 35 U.S.C. 154(b) by 254 days.

(21) Appl. No.: 18/408,460

(22) Filed: Jan. 9, 2024

(65) Prior Publication Data

US 2024/0230432 A1 Jul. 11, 2024

(30) Foreign Application Priority Data

Jan. 10, 2023 (KR) ........................ 10-2023-0003580

(51) Int. Cl.

*G01L 1/22* (2006.01)
*G01L 5/10* (2020.01)
*A61B 34/20* (2016.01)

(52) U.S. Cl.

CPC .............. *G01L 1/2287* (2013.01); *G01L 5/10* (2013.01); *A61B 2034/2061* (2016.02)

(58) Field of Classification Search

CPC . G01L 1/2287; G01L 5/10; A61B 2034/2061; A61B 5/6804; A61B 5/01; A61B 5/021; A61B 5/02438; A61B 5/27; A61B 5/28; A61B 2562/12

See application file for complete search history.

(56) References Cited

U.S. PATENT DOCUMENTS 9,853,219 B2 12/2017 Lee et al.
9,970,832 B2 * 5/2018 Hong .................... G01L 1/2287
11,217,366 B2 1/2022 Baughman et al.
11,402,282 B2 * 8/2022 Yoshida .................... G01L 1/16

(Continued)

FOREIGN PATENT DOCUMENTS

CN 112957030 A * 6/2021 ........... A61B 5/1075
KR 20150078803 A * 7/2015 ........... H01B 7/0208

(Continued)

OTHER PUBLICATIONS

CN-112957030-A (Year: 2021).*

(Continued)

*Primary Examiner* — Fatemeh Esfandiari Nia

(74) *Attorney, Agent, or Firm* — BROADVIEW IP LAW, PC

(57) ABSTRACT

The present exemplary embodiments propose a fiber-based strain sensor including: at least one first electric conductive line including a first flexible part having electric conductivity and at least one second electric conductive line which is woven to be in partially contact with the first electric conductive line, includes a second flexible part having electric conductivity, and is implemented to conduct electricity with the first flexible part having electric conductivity in a stretched state.

9 Claims, 12 Drawing Sheets

(56) References Cited

U.S. PATENT DOCUMENTS

| | | | | |
|---|---|---|---|---|
| 2015/0201694 | A1* | 7/2015 | Boyce | G08B 21/182<br>340/539.12 |
| 2018/0328708 | A1* | 11/2018 | Okumiya | G01L 1/2287 |
| 2020/0003638 | A1* | 1/2020 | Visell | G01L 1/18 |
| 2020/0063296 | A1 | 2/2020 | Ozden et al. | |

FOREIGN PATENT DOCUMENTS

| | | | | |
|---|---|---|---|---|
| KR | 10-2018-0085696 | A | 7/2018 | |
| KR | 102026011 | B1 * | 9/2019 | G01L 5/00 |
| KR | 10-2048563 | B1 | 11/2019 | |
| KR | 10-2022-0102784 | A | 7/2022 | |
| KR | 10-2418327 | B1 | 7/2022 | |
| WO | WO-2013085038 | A1 * | 6/2013 | A61B 5/03 |

OTHER PUBLICATIONS

KR-102026011-B1 (Year: 2019).*

WO-2013085038-A1 (Year: 2013).*

Vervuurt, Rene HJ, et al. "Uniform atomic layer deposition of Al2O3 on graphene by reversible hydrogen plasma functionalization." Chemistry of Materials 29.5 (2017): 2090-2100. (Year: 2017).*

KR-20150078803-A (Year: 2015).*

Office Action for KR 10-2023-0003580 by Korean Intellectual Property Office dated Mar. 17, 2025.

Lee, Jaehong et al. (2021), "Stretchable and suturable fibre sensors for wireless monitoring of connective tissue strain", nature electronics, vol. 4, pp. 291-301, doi.org/10.1038/s41928-021-00557-1.

* cited by examiner

Resistance (Ω)

Time (s)

11.8 mHz 33.5 mHz 59.5 mHz 84.7 mHz (c)

Resistance (Ω)

Cycle

FIBER-BASED STRAIN SENSORS AND METHOD OF MANUFACTURING THE SAME

CROSS-REFERENCE TO RELATED APPLICATIONS

This application claims priority to and the benefit of Korean Patent Application No. 10-2023-0003580 filed in the Korean Intellectual Property Office on Jan. 10, 2023, the entire contents of which are incorporated herein by reference.

TECHNICAL FIELD

The present disclosure relates to a fiber-based strain sensor and a method for manufacturing the same, and more particularly, to a fiber-based strain sensor which senses a stretched state to conduct electricity and a method for manufacturing the same.

BACKGROUND ART

The contents described in this section merely provide background information on the present exemplary embodiment but do not constitute the related art.

As a monitoring system which can collect biometric data in everyday life, a wearable device that is attached or worn on the body to regularly check and collect health indicators, such as a pulse, a blood pressure, a temperature, and an electrocardiogram generated in the human body, is representative. Such a wearable device needs to measure various signals while minimizing discomfort during the wearing, but most popular devices on the market are accessory types, such as smart watches or smart bands so that due to limitations in materials which configure electronic devices, there is a problem in that the wearable device is limited to a wrist type in the form of a hard accessary type.

Further, a wearable device which is applicable to various parts of a body of the user with a high elasticity is implemented as smart clothing and various sensors and semiconductor devices are mounted in cutting-edge fibers/materials to implement various monitoring systems which monitor motions, postures, and stimulation as well as the wearer's biological signals. However, there is a problem in that a low-power technique for operating the regular monitoring while minimizing the power consumption is necessary.

SUMMARY OF THE INVENTION

A main object of exemplary embodiments of the present disclosure is to apply a conductive fiber in which resistance is lowered only upon stretching by a strain sensor having a negative gauge-factor (N-GF) which also serves as a wiring line to flow current to smart clothing to transmit a biometric signal.

Other and further objects of the present disclosure which are not specifically described can be further considered within the scope easily deduced from the following detailed description and the effect.

According to an aspect of the present embodiment, the present disclosure proposes a fiber-based strain sensor including: at least one first electric conductive line including a first flexible part having electric conductivity and at least one second electric conductive line which is woven to be in partially contact with the first electric conductive line, includes a second flexible part having electric conductivity, and is implemented to conduct electricity with the first flexible part having electric conductivity in a stretched state.

Desirably, the first electric conductive line and the second electric conductive line are woven to be twisted and a first node connected to the first electric conductive line and a second node connected to the second electric conductive line forms a mutual resistance which is formed to be equal to or lower than a predetermined resistance according to a stretched state.

Desirably, an insulator is formed in the first flexible part or in the second flexible part.

Desirably, a degree of resistance change is adjusted by adjusting a number of times of twisting the at least one first electric conductive line and the at least one second electric conductive line or a degree of twisting the at least one first electric conductive line and the at least one second electric conductive line.

Desirably, in the first electric conductive line or the second electric conductive line, a conductive part having the electric conductivity is formed by depositing metal nano particles in the first flexible part or the second flexible part and the insulator is formed by depositing an insulating thin film on a surface of the conductive part and the insulating thin film is cured by selective irradiation of ultraviolet ray or laser or selective thermal treatment.

Desirably, the first flexible part and the second flexible part include at least one of polyurethane, styrene-butadiene-styrene (SBS), styrene butadiene rubber (SBR), and polydimethylsiloxane (PDMS) which are formed of polymer materials and the conductive part includes at least one of metal material implemented by nano particles, a conductive organic material, and nano materials.

Desirably, the insulator includes at least one of organic materials which form an insulator characteristic, such as SU-8, polyimide, PVA, PMMA, or CYTOP or oxide, such as SiOx or HfOx.

Desirably, the insulator adjusts a degree of causing a crack according to stretching, by adjusting a modulus, a thickness, or a hardness by means of curing.

Desirably, the fiber-based strain sensor is implemented to be applied to a stretchable device and the stretchable device is applied in a position in which the fiber-based strain sensor is stretchable in a length direction.

According to another aspect of the present disclosure, the present disclosure provides a monitoring system including a fiber-based strain sensor including: at least one first electric conductive line including a first flexible part having electric conductivity and at least one second electric conductive line which is woven to be in partially contact with the first electric conductive line, includes a second flexible part having electric conductivity, and is implemented to conduct electricity with the first flexible part having electric conductivity in a stretched state, a stretchable device to which the fiber-based strain sensor is applied and which is implemented to be stretchable by movement, and a monitoring device which receives current generated upon stretching in a wired or wireless method to monitor the state of the stretchable device.

Desirably, the stretchable device is implemented to apply the fiber-based strain sensor to a position to be stretchable in a length direction so that the first electric conductive line and the second electric conductive line conduct electricity upon stretching and when the electricity is conducted by the stretching, the monitoring device predicts a shape of the stretchable device to provide a feedback in real time.

According to still another aspect of the present disclosure, a manufacturing method for manufacturing a fiber-based strain sensor includes a step of forming a conductive part having an electric conductivity by depositing metal nano particles in a flexible part including elasticity; and a step of weaving at least two electric conductive lines to be in partially contact with each other when the electric conductive lines are stretched, to conduct electricity.

Desirably, the manufacturing method further includes a step of forming an insulator by depositing an insulating thin film on a surface of the conductive part, and in the step of forming an insulator, the insulator is formed by curing through selective irradiation of ultraviolet ray or laser or selective thermal treatment.

As described above, according to the exemplary embodiments of the present disclosure, the present disclosure minimizes power consumption and performs the regular monitoring while providing a high elasticity to be mounted on a body of the wearer.

Even if the effects are not explicitly mentioned here, the effects described in the following specification which are expected by the technical features of the present disclosure and their potential effects are handled as described in the specification of the present disclosure.

BRIEF DESCRIPTION OF THE DRAWINGS

FIG. 1 is a view illustrating the manufacturing of a single electric conductive line according to an exemplary embodiment of the present disclosure;

FIG. 3 is a view illustrating a fiber-based strain sensor by twisting two electric conductive lines according to an exemplary embodiment of the present disclosure;

FIG. 4 is a view illustrating a resistance change per number of times of twisting two electric conductive lines according to an exemplary embodiment of the present disclosure;

DETAILED DESCRIPTION OF THE EMBODIMENT

Figure 2:
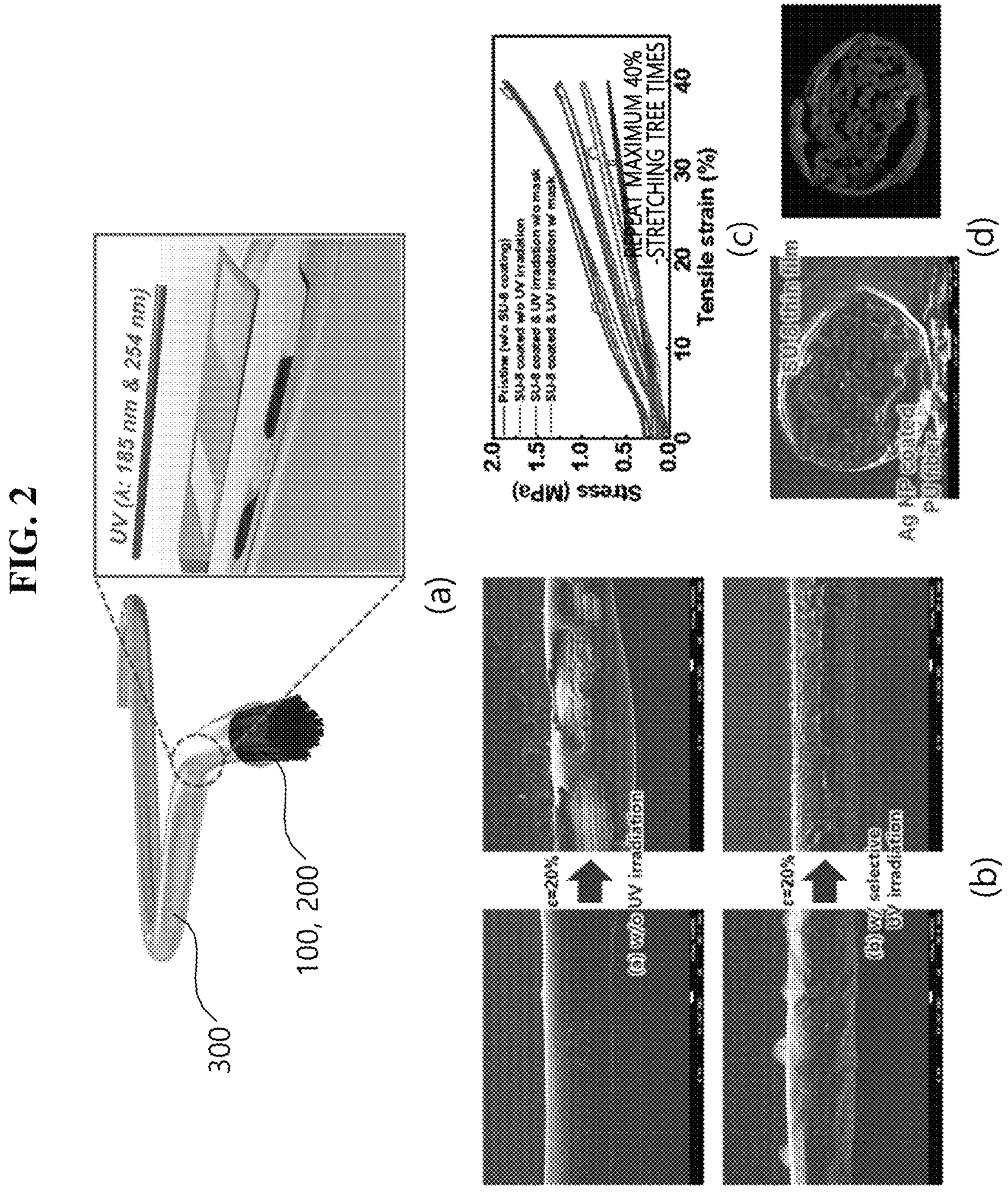
FIG. 2 is a view illustrating analysis after insulation film deposition and selective UV irradiation according to an exemplary embodiment of the present disclosure.

Hereinafter, in the description of the present disclosure, a detailed description of the related known functions will be omitted if it is determined that the gist of the present disclosure may be unnecessarily blurred as it is obvious to those skilled in the art and some exemplary embodiments of the present disclosure will be described in detail with reference to exemplary drawings. However, the present invention can be realized in various different forms, and is not limited to the exemplary embodiments described herein. In order to clearly describe the present invention, a part which may obscure the present invention may be omitted and like reference numerals denote like components.

A term of and/or includes combination of a plurality of related elements or any one of the plurality of related elements.

It should be understood that, when it is described that an element is “coupled” or “connected” to another element, the element may be directly coupled or directly connected to the other element or coupled or connected to the other element through a third element.

Further, such as “module” and a “unit”, suffixes for components used in the following description are given or mixed and used by considering easiness in preparing a specification and do not have a meaning or role distinguished from each other in themselves.

Terms such as first or second may be used to describe various components but the components are not limited by the above terms. The above terms are used only to distinguish one component from the other component.

The present invention relates to a fiber-based strain sensor and a method for manufacturing the same.

Digital healthcare is an industry which provides advanced patient-customized medical services and health care products and services for improving health by utilizing an information and communication technology and those who have help from the digital healthcare are people with chronic diseases (high blood pressure, diabetes, chronic respiratory disease, chronic disc diseases) who must always manage their health conditions. The most important technology for them is a technology for a monitoring system which collects biometric data in the everyday life and a wearable device that is attached or worn on the body to regularly check and collect health indicators, such as a pulse, a blood pressure, a temperature, and an electrocardiogram generated in the human body, is representative.

Such a wearable device needs to measure various signals while minimizing discomfort during the wearing, but most popular devices on the market are accessory types, such as smart watches or smart bands, and due to limitations in materials which configure electronic devices, there is a problem in that the wearable device is limited to a wrist type as a hard accessary type. Accordingly, in order to overcome the problem, “smart clothing” is highly anticipated as a representative next-generation wearable device which has a high elasticity and is applicable to various parts of the body. Various sensors and semiconductor devices are mounted in cutting-edge fibers/materials to implement various monitoring systems which monitor motions, postures, and stimulations in the body as well as the wearer’s biological signals to have greater applicability.

However, the development of the monitoring system based on the smart clothing described above has a technical obstacle in that it requires a low-power technology to operate the regular monitoring while minimizing the power consumption. In order to overcome this obstacle, various low-power technologies are being studied, but these technologies are focusing only on developing ultra-small and high capacity battery technologies rather than developing the low-power sensor or semiconductor technology.

Accordingly, in order to implement ultra-low power health monitoring system which is applicable to smart clothing, the present disclosure is implemented by a strain sensor having a negative gauge factor (N-GF) which also serves as a wiring line by overcoming a physical limitation of the existing device.

Generally, under a given strain rate, the conductive fiber has a positive gauge-factor (P-GF) that increases the electrical resistance due to the crack. However, the fiber-based strain sensor 1 according to the present disclosure has a N-GF so that when a conductive fiber in which the resistance is lowered only upon the stretching to flow current is manufactured, a low-power system which operates only when there is a problem in the physical function or it is stretched to transmit a biometric signal, such as a switchable monitoring system which operates only in a circumstance that an organ swells (for example, a bladder expansion or heart relaxation) when it is inserted into the body, can be implemented.

Further, a display technology which brings about changes in form-factor is currently commercialized from curved or bendable fixed flexible displays which are a first stage to rollable and foldable single axis variable flexible displays which are a second stage. Further, stretchable displays, also known as freeform displays are emerging as a next-generation form-factor innovative display which is a third stage. Among them, a representative stretchable display which is freely expandable and contractible is a fiber-based clothing display and this display goes beyond attaching a flexible display to clothing and is expected to create a new concept market where clothing and displays are integrated by means of the development of the electronic fibers. However, unlike the existing flexible display, such a clothing display is a stretchable display, so that there is a problem in that resolution/luminance is changed due to the increase in the interval between pixels, compared to the same number of pixels, upon stretching, to cause the image distortion. Therefore, a solution therefor is urgently needed.

Due to a fiber-based strain sensor which includes a material whose resistive characteristic is changed according to a tension applied to the display, a light emitting diode (hidden pixel) which is not driven before stretching the display is controlled to emit light after stretching the display so that a stretchable clothing display which suppresses the image distortion due to the change in resolution and luminance even though the display is stretched can be implemented. A wiring line having a N-GF of the related art does not have a large N-GF or resistance change rate which changes from a nonconductor to a conductor and there is no example which is applied to the fiber.

Therefore, in order to solve the above-described problem, the fiber-based strain sensor 1 may be implemented by a conductive fiber which has a negative gauge-factor (N-GF) to lower the resistance only upon stretching to flow current.

Figure 1:
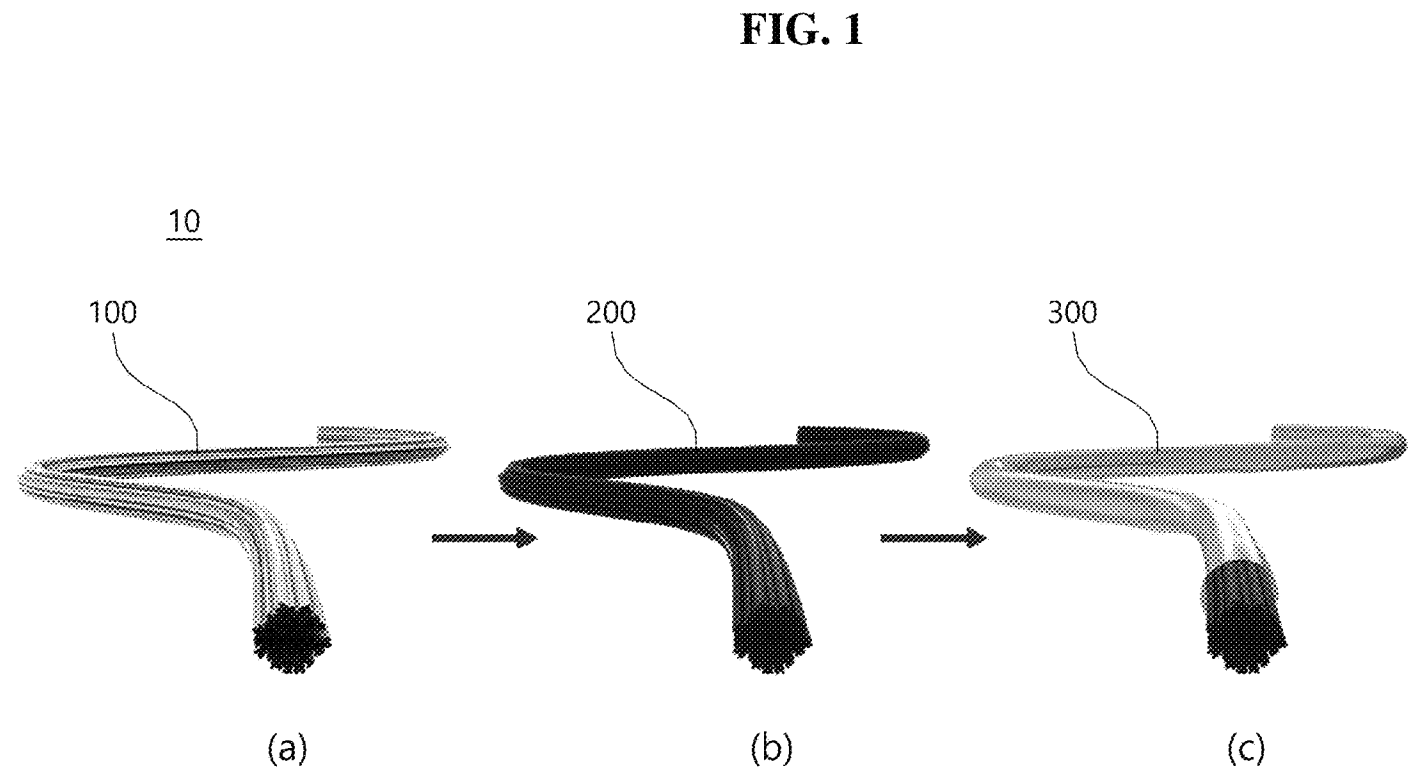

FIG. 1 is a view illustrating the manufacturing of a single electric conductive line according to an exemplary embodiment of the present disclosure.

The fiber-based strain sensor 1 includes a first electric conductive line 10*a* and a second electric conductive line 10*b*.

Referring to FIG. 1, the electric conductive line 10 includes a flexible part 100, a conductive part 200, and an insulator 300. The electric conductive line 10 may omit some components among various components which are exemplarily illustrated in FIG. 1 or may further include other component.

The electric conductive line 10 includes the flexible part 100 having electric conductivity.

The fiber-based strain sensor 1 includes at least one first electric conductive line 10 including a first flexible part having electric conductivity and at least one second electric conductive line 10*b* which is woven to be in partially contact with the first electric conductive line 10*a*, includes a second flexible part having electric conductivity, and is implemented to be electrically conducted with the first flexible part having electric conductivity in a stretched state.

The first electric conductive line 10*a* or the second electric conductive line 10*b* further includes an insulator 300 which is formed on a surface of the flexible part 100 having electric conductivity.

In the fiber-based strain sensor 1, the first electric conductive line 10*a* and the second electric conductive line 10*b* are woven to be twisted and a first node connected to the first electric conductive line 10*a* and a second node connected to the second electric conductive line 10*b* form a mutual resistance which is formed to be equal to or lower than a predetermined resistance according to a stretched state.

The fiber-based strain sensor 1 is implemented to adjust a degree of resistance change by adjusting the number or degree of twisting at least one first electric conductive line 10*a* and at least one second electric conductive line 10*b*.

In the first electric conductive line 10*a* or the second electric conductive line 10*b*, a conductive part 200 having electric conductivity is formed on the surface of the flexible part 100 by deposition of metal nano particles and an insulator 300 is formed on the surface of the conductive part by deposition of an insulating thin film. Here, the insulating thin film is cured by selective irradiation of ultra violet or laser or selective heat treatment and for example, is formed by selectively irradiating ultraviolet curing (UV-curing).

The flexible part 100 includes at least one of polyurethane, styrene-butadiene-styrene (SBS), styrene butadiene rubber (SBR), and polydimethylsiloxane (PDMS) which are formed of polymer materials.

The conductive part 200 includes at least one of metal materials, conductive organic materials, and nano materials which are implemented by nano particles.

The insulator 300 includes at least one of organic materials which form an insulator characteristic, such as SU-8, polyimide, PVA, PMMA, or CYTOP or oxide, such as SiOx or HfOx.

The insulator 300 adjusts a degree of causing a crack according to strain, by adjusting a modulus, a thickness, or a hardness by means of curing.

The fiber-based strain sensor 1 is implemented to be applied to a stretchable device. Here, the stretchable device is applied to a position in which the fiber-based strain sensor 1 is stretchable in a length direction.

Accordingly, the fiber-based strain sensor 1 may form a wiring electrode having a N-GF in which current flows only upon stretching by depositing a thin film having an insulation characteristic on two conductive fibers, and then twisting two elements to finely adjust a density and a size of the crack according to the strain.

FIG. 2 is a view illustrating analysis after insulation film deposition and selective UV irradiation according to an exemplary embodiment of the present disclosure.

Referring to FIG. 2, the fiber-based strain sensor 1 is formed by depositing Ag nanoparticle (AgNP) which is a conductive material on a surface of a polyurethane (PU) fiber which represents an elastic fiber and then depositing a SU-8 insulating film thereon and selectively irradiating UV.

Referring to FIG. 2A, the fiber-based strain sensor 1 further performs selective curing by UV irradiation of an insulator.

FIG. 2B is a view illustrating a crack formation pattern upon stretching depending on the presence or absence of UV irradiation according to an exemplary embodiment of the present disclosure, FIG. 2C is a graph illustrating a strain stress measurement result by a force sensor according to an exemplary embodiment of the present disclosure, and FIG. 2D is a view illustrating a cross-section of a fiber-based strain sensor in which a surface is deposited with a SU-8 insulating film, according to an exemplary embodiment of the present disclosure.

Figure 3:
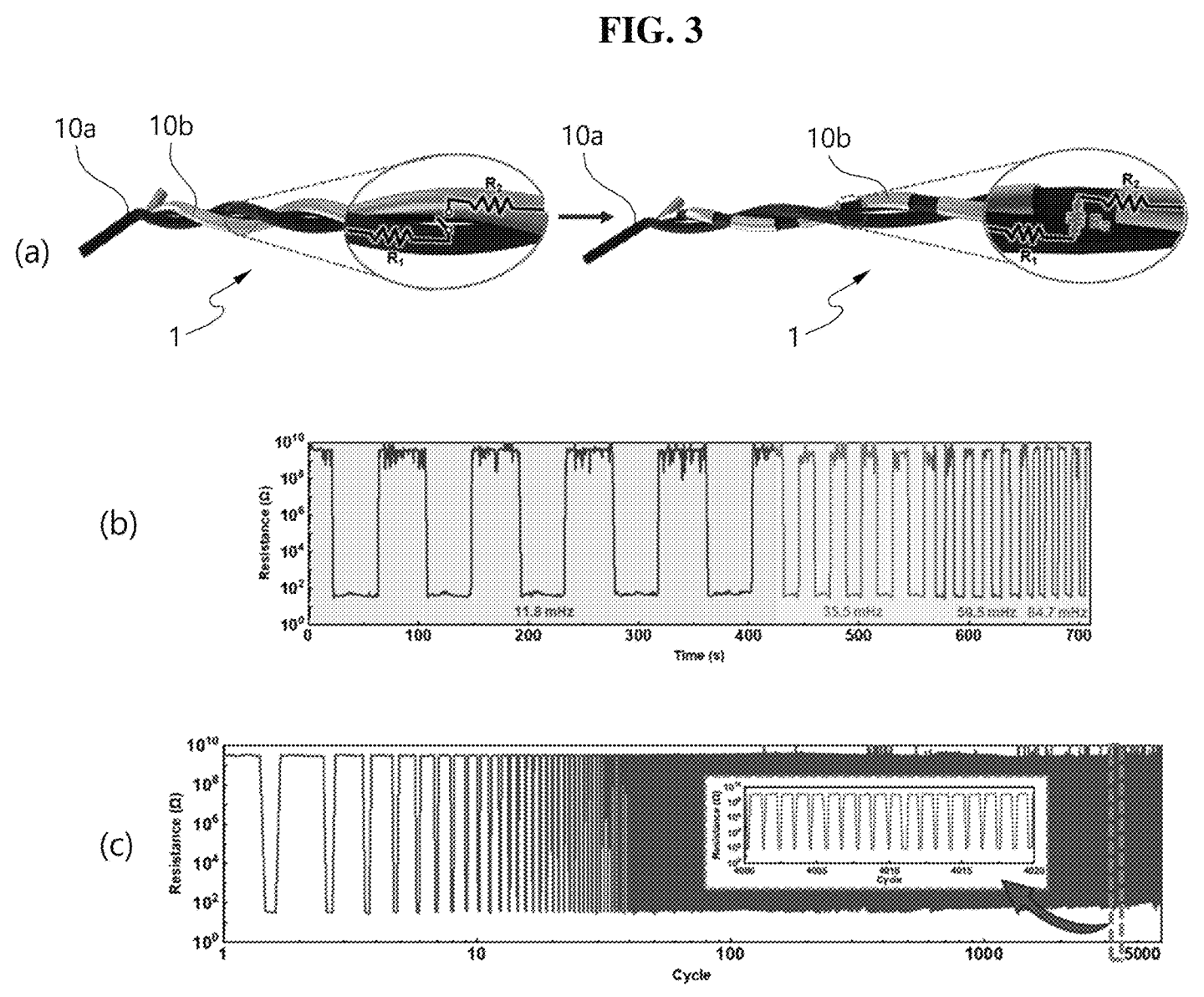

FIG. 3 is a view illustrating a fiber-based strain sensor by twisting two electric conductive lines according to an exemplary embodiment of the present disclosure.

The fiber-based strain sensor 1 is implemented by twisting two electric conductive lines are twisted to have N-GF so that cracks are in contact with each other upon stretching. Specifically, when the first electric conductive line 10*a* and the second electric conductive line 10*b* are stretched, the first electric conductive line 10*a* and the second electric conductive line 10*b* are in contact with each other and the resistors are connected to each other.

Referring to FIG. 3, a sensing result of a fiber-based strain sensor 1 manufactured by twisting SU-8/AgNP coated PU fiber is confirmed.

FIG. 3B is a view illustrating a change in resistance (repetition of 20%-stretching) of a device according to a stretching speed according to an exemplary embodiment of the present disclosure and FIG. 3C is a view illustrating a result of measuring a predetermined number of repetitions of 20% stretching according to an exemplary embodiment of the present disclosure.

Figure 4:
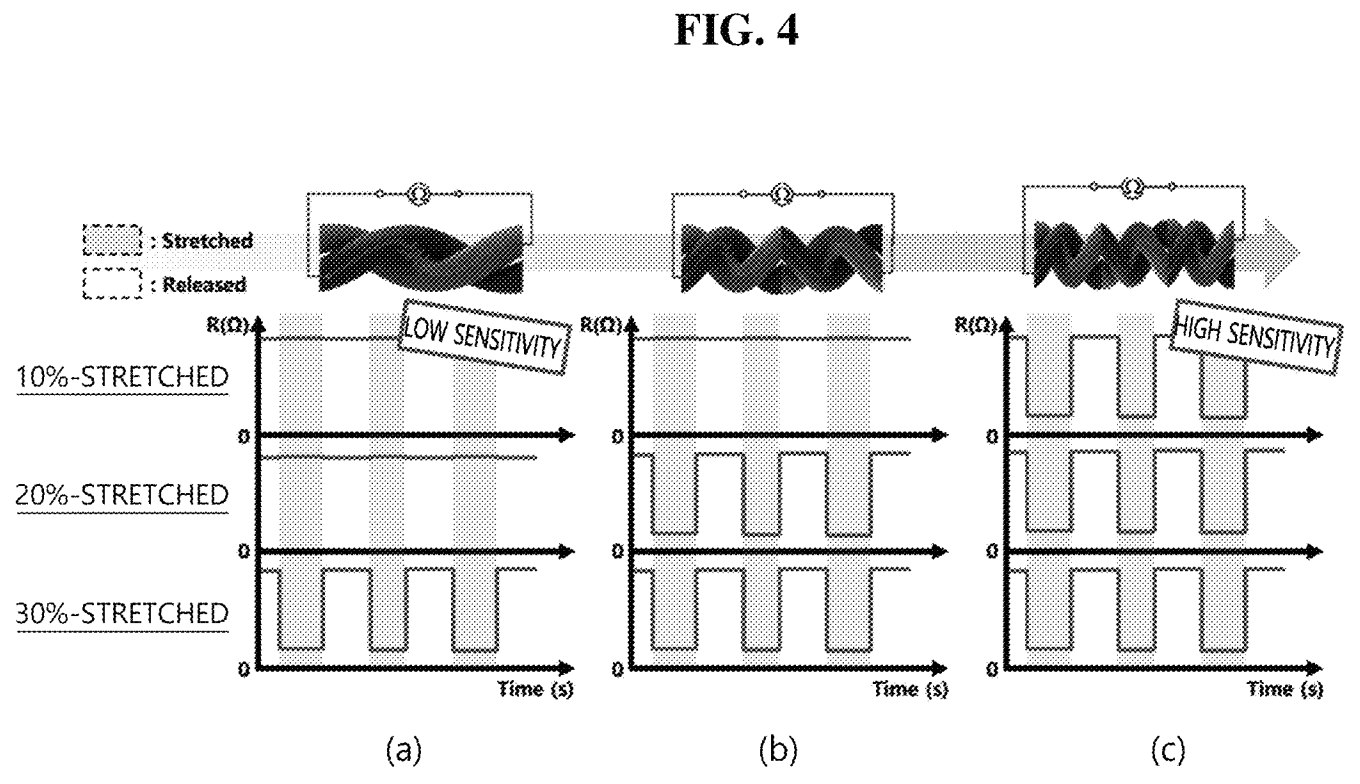

FIG. 4 is a view illustrating a resistance change per number of times of twisting two electric conductive lines according to an exemplary embodiment of the present disclosure.

Referring to FIG. 4, the fiber-based strain sensor 1 is implemented to adjust the resistance-change sensitivity by adjusting a number of twisting the electric conductive line when the electric conductive line is woven.

FIG. 4A is a view illustrating 10%-stretched, 20%-stretched, and 30%-stretched when it is twisted once, according to an exemplary embodiment of the present disclosure, FIG. 4B is a view illustrating 10%-stretched, 20%-stretched, and 30%-stretched when it is twisted twice, according to an exemplary embodiment of the present disclosure, and FIG. 4C is a view illustrating 10%-stretched, 20%-stretched, and 30%-stretched when it is twisted three times, according to an exemplary embodiment of the present disclosure.

Referring to FIG. 4, it is confirmed that when it is twisted once, the fiber-based strain sensor 1 forms a low sensitivity and when it is twisted three times, the fiber-based strain sensor 1 forms a high sensitivity.

Figure 5:
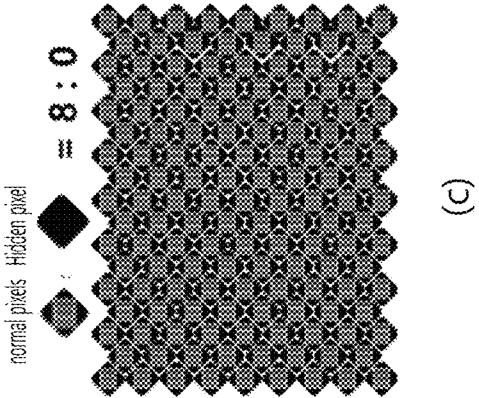
FIG. 5 is a view illustrating a number of hidden pixels according to a strain of two electric conductive lines according to an exemplary embodiment of the present disclosure.
Figure 5:
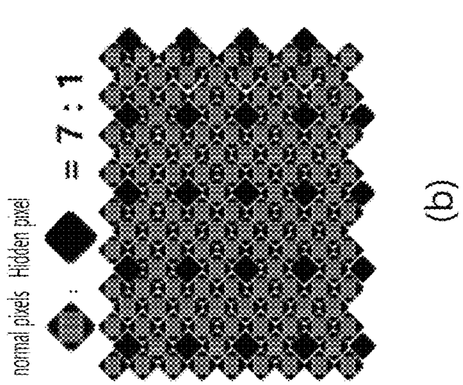
Figure 5:
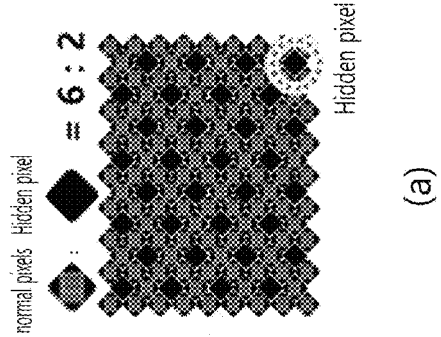

FIG. 5 is a view illustrating a number of hidden pixels according to a strain of two electric conductive lines according to an exemplary embodiment of the present disclosure.

Referring to FIG. 5A, when the fiber-based strain sensor 1 is 10%-stretched, it is confirmed that a ratio of normal pixels and hidden pixels is 6:2.

Referring to FIG. 5B, when the fiber-based strain sensor 1 is 20%-stretched, it is confirmed that a ratio of normal pixels and hidden pixels is 7:1.

Referring to FIG. 5C, when the fiber-based strain sensor 1 is 30%-stretched, it is confirmed that a ratio of normal pixels and hidden pixels is 8:0.

By doing this, the fiber-based strain sensor 1 adjusts a number of hidden pixels which is increased according to a strain.

Figure 6:
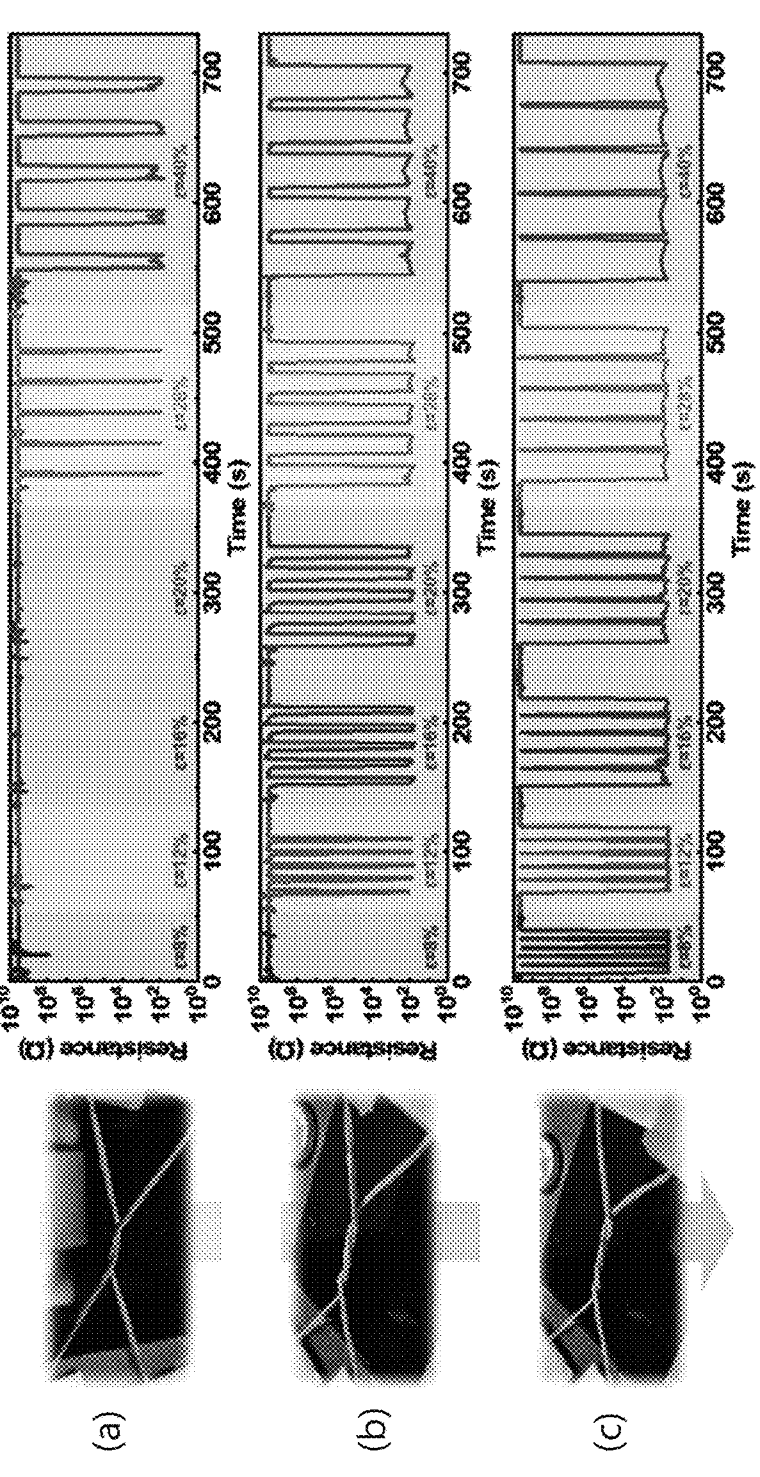
FIG. 6 is a view illustrating a resistance change per strain by adjusting a number of times of twisting two electric conductive lines according to an exemplary embodiment of the present disclosure.

FIG. 6 is a view illustrating a resistance change per strain by adjusting a number of times of twisting two electric conductive lines according to an exemplary embodiment of the present disclosure.

Referring to FIG. 6, a resistance change result (five times repeated) of a device according to a strain is confirmed by adjusting a number of times of twisting SU-8/AgNP coated PU fiber.

Figure 7:
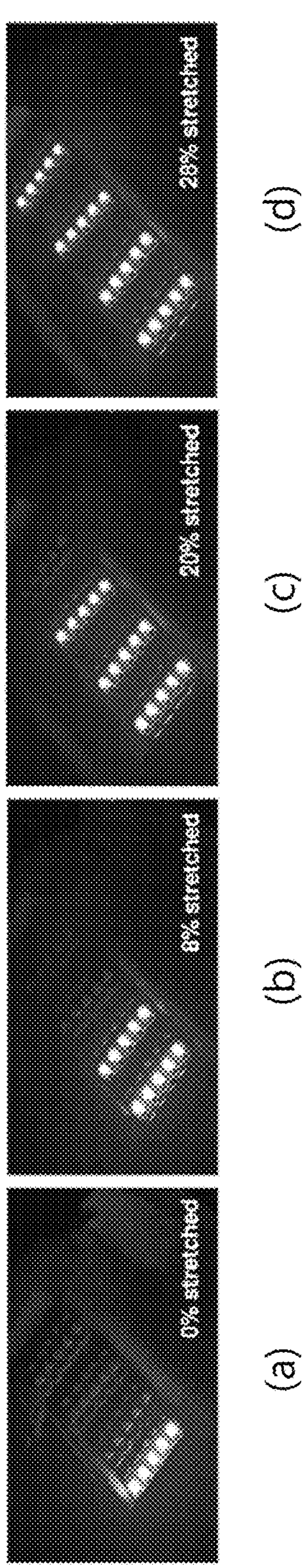
FIG. 7 is a view illustrating that a fiber based strain sensor according to the exemplary embodiment of the present disclosure is applied to an LED array.

FIG. 7 is a view illustrating that a fiber based strain sensor according to the exemplary embodiment of the present disclosure is applied to an LED array.

Referring to FIG. 7, it is confirmed that a reaction of the fiber-based strain sensor 1 in an LED array spreads in a stretching direction depending on the strain.

Figure 8:
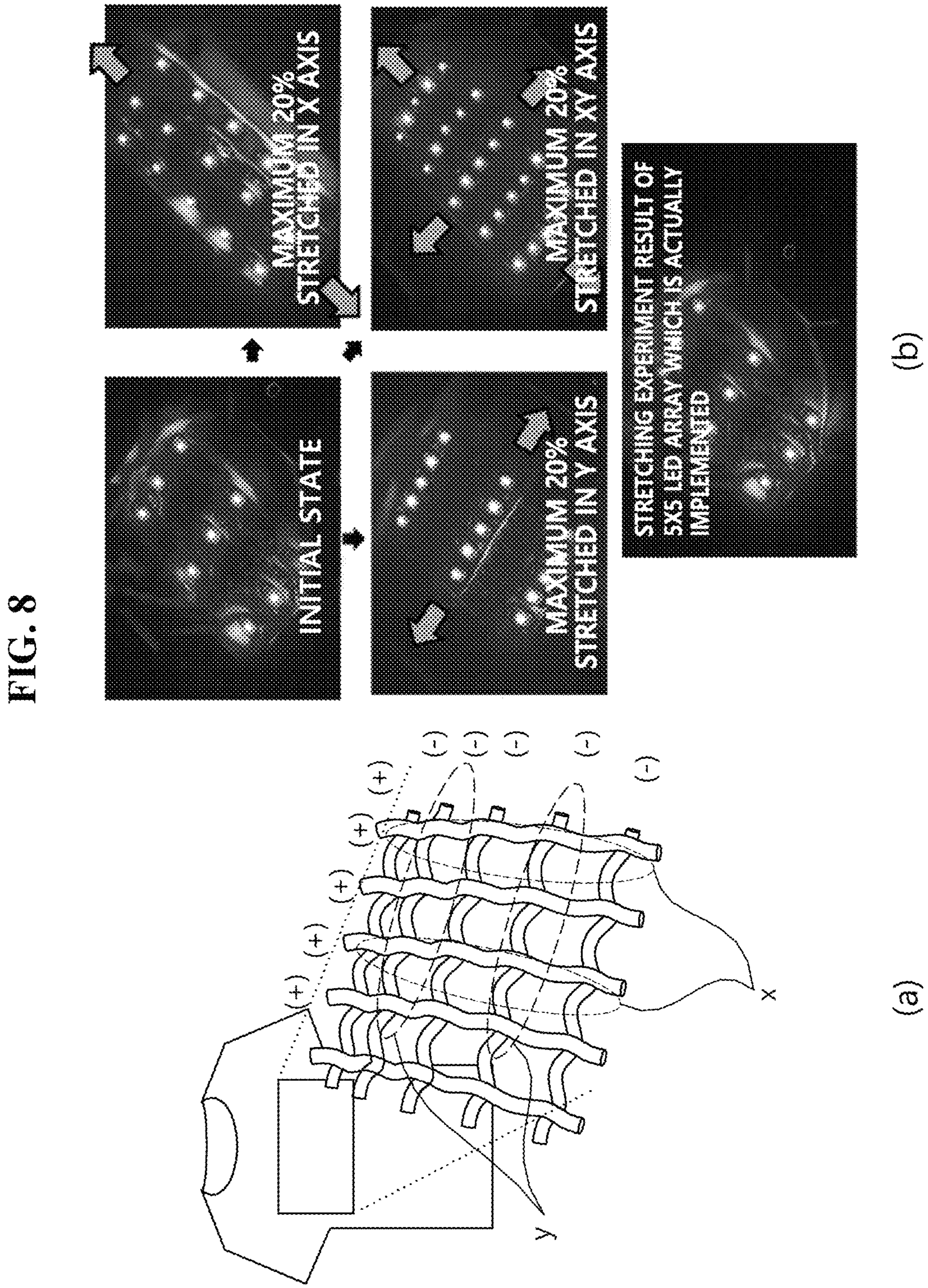
FIG. 8 is a view illustrating a monitoring system to which a fiber-based strain sensor according to a first exemplary embodiment of the present disclosure is applied.
Figure 9:
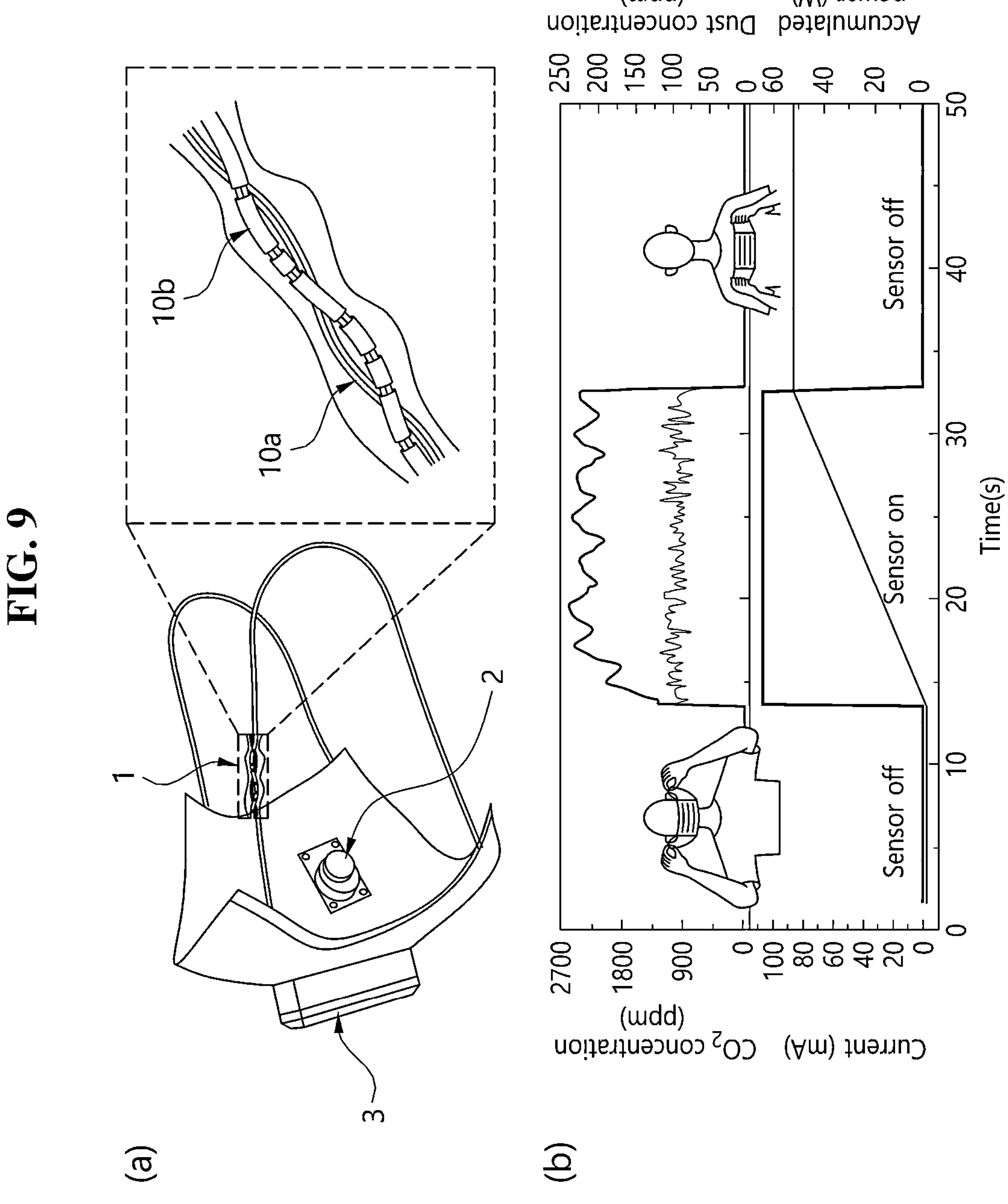
FIG. 9 is a view illustrating a monitoring system to which a fiber-based strain sensor according to a second exemplary embodiment of the present disclosure is applied.
Figure 10:
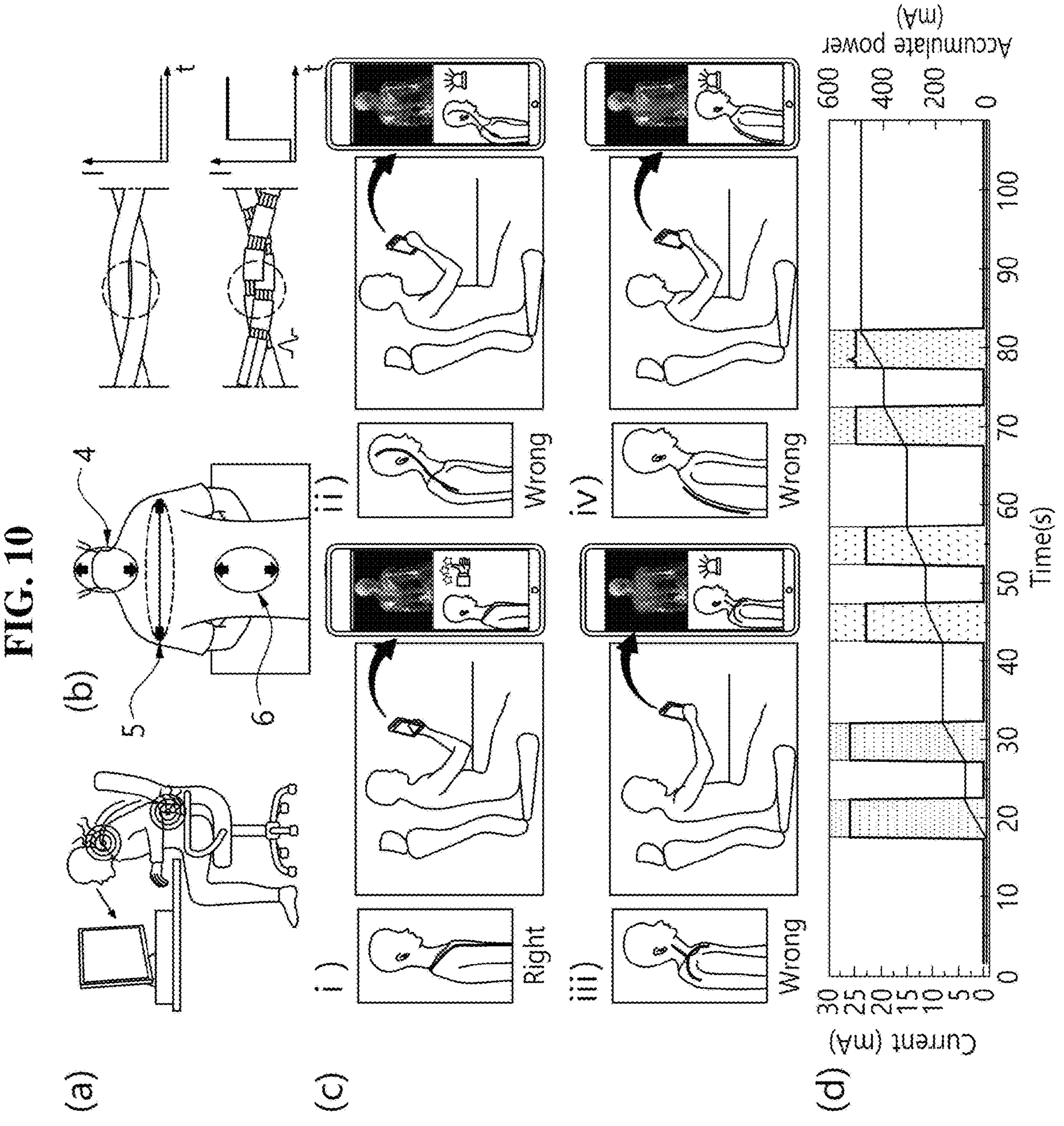
FIG. 10 is a view illustrating a monitoring system to which a fiber-based strain sensor according to a third exemplary embodiment of the present disclosure is applied.

FIGS. 8 to 10 are views illustrating a monitoring system to which a fiber-based strain sensor according to an exemplary embodiment of the present disclosure is applied.

The monitoring system includes a fiber-based strain sensor, a stretchable device, and a monitoring device.

A fiber-based strain sensor includes at least one first electric conductive line including a first flexible part having electric conductivity and at least one second electric conductive line which is woven to be in partially contact with the first electric conductive line, includes a second flexible part having electric conductivity, and is implemented to conduct electricity with the first flexible part having electric conductivity in a stretched state.

The fiber-based strain sensor is applied to the stretchable device and the stretchable device is implemented to be stretched by the movement.

The monitoring device receives current generated upon stretching in a wired or wireless method to monitor the state of the stretchable device.

FIG. 8 is a view illustrating a monitoring system to which a fiber-based strain sensor according to a first exemplary embodiment of the present disclosure is applied.

According to a first exemplary embodiment, the fiber-based strain sensor 1 is applied to a stretchable clothing display.

According to the exemplary embodiment of the present disclosure, when the stretchable clothing display is stretched in a bi-axial direction, a hidden pixel for supplementing a resolution may be applied. At this time, the hidden pixel for supplementing the resolution is implemented by an LED array, but is not necessarily limited thereto.

The stretchable clothing display is implemented such that a (+) electrode which is always connected and a (+) electrode which is connected to the fiber-based strain sensor are disposed to intersect each other and a (−) electrode which is always connected and a (−) electrode which is connected to the fiber-based strain sensor are disposed to intersect each other.

X represents a hidden pixel in an x-axis direction which is turned on upon the x-axis stretching and y represents a hidden pixel in a y-axis direction which is turned on upon the y-axis stretching.

FIG. 9 is a view illustrating a monitoring system to which a fiber-based strain sensor according to a second exemplary embodiment of the present disclosure is applied.

According to a second exemplary embodiment, the fiber-based strain sensor 1 is applied to a healthcare monitoring system. For example, the fiber-based strain sensor 1 is applied to a low-power smart mask in which a respiration detecting sensor is embedded.

According to the exemplary embodiment of the present disclosure, the fiber-based strain sensor 1 is applied to an ear loop of the mask, but is not necessarily limited thereto.

Referring to FIG. 9, a gas-sensor based ultra-low power monitoring system is implemented by inserting a manufactured fiber-based strain sensor 1 into a rubber band mask string as a wiring line and operates only when the mask is worn to have a standby power of 0.

At this time, the mask in the healthcare monitoring system is implemented to monitor a breathing habit or a health condition of the user through the CO2 sensor 2 and measure a concentration of fine dust through a fine dust sensor 3.

FIG. 10 is a view illustrating a monitoring system to which a fiber-based strain sensor according to a third exemplary embodiment of the present disclosure is applied.

According to a third exemplary embodiment, the fiber-based strain sensor 1 is applied to a healthcare monitoring system. For example, the fiber-based strain sensor 1 is applied to a real-time low power posture monitoring smart clothing for correcting the posture.

Referring to FIG. 10, the manufactured fiber-based strain sensor 1 is implemented to be inserted into neck, shoulder, and waist to flow current only in a wrong posture and display a notification on a smart phone application according to the current value. At this time, in a correct posture, the current does not flow so that there is no stand-by power consumption.

The fiber-based strain sensor 1 is implemented to be detachable to match for every wearer, but is not necessarily limited thereto.

Figure 11:
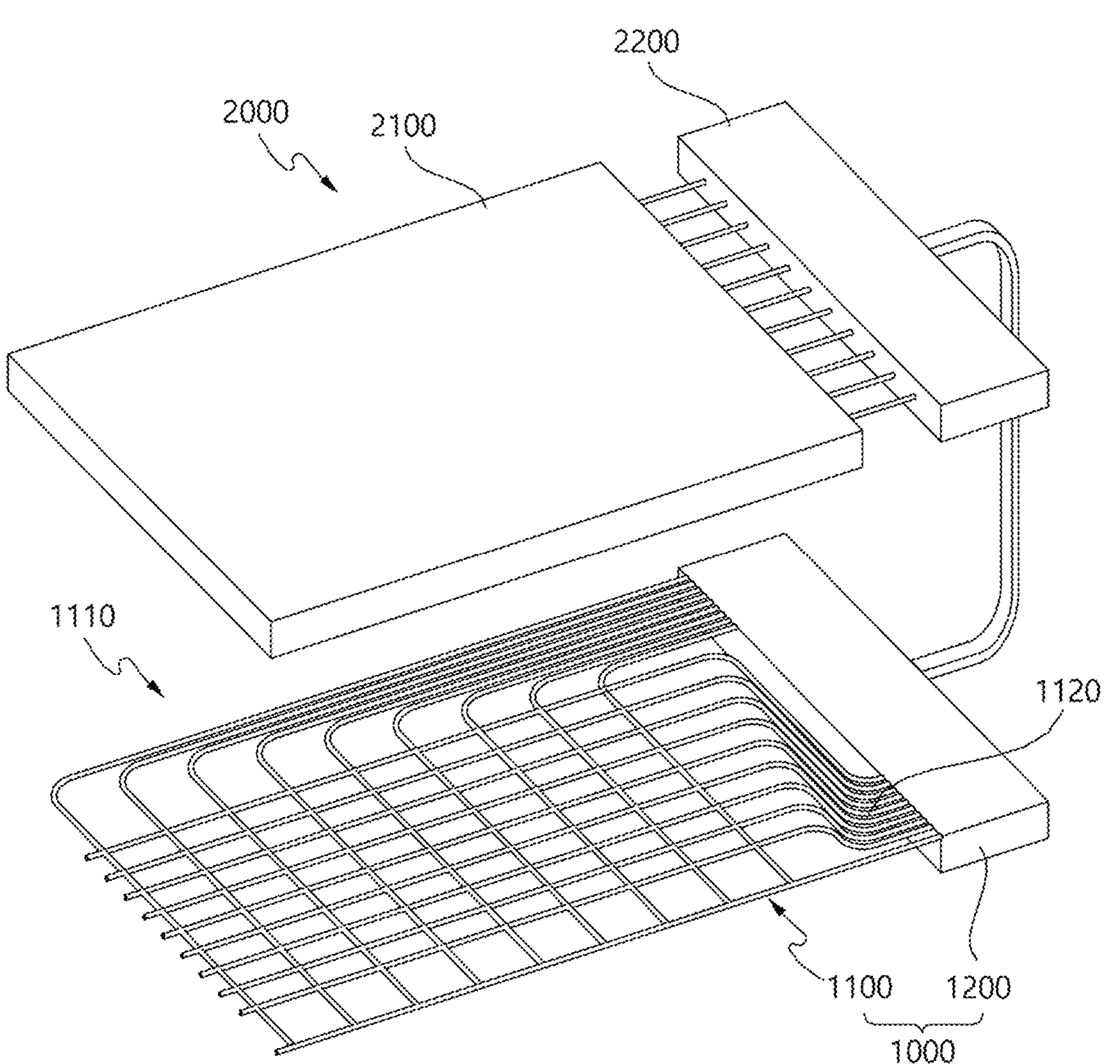
FIG. 11 is a diagram of a monitoring system according to still another exemplary embodiment of the present disclosure.

FIG. 11 is a diagram of a monitoring system according to still another exemplary embodiment of the present disclosure.

Referring to FIG. 11, the monitoring system includes a fiber-based strain sensor 1000, a display unit 2000, a power source unit (not illustrated), and a housing (not illustrated). The monitoring system may omit some components among various components which are exemplarily illustrated in FIG. 11 or may further include other component.

The fiber-based strain sensor 1000 includes a sensor array 1100 in which conductive fibers of the present disclosure are disposed and a first controller 1200. The sensor array 1100 has a structure in which conductive twist sensor lines in which the first electric conductive line and the second electric conductive line are coupled to be twisted intersect each other. The sensor array is also implemented in various arrangement forms, such as one-dimensional arrangement or three-dimensional arrangement, rather than two-dimensional arrangement. An electric signal from each of conductive twist sensor lines is collected by the first conductive bus line 1110 and the second conductive bus line 1120 and is transmitted to the first controller 1200.

The first controller 1200 analyzes the collected electric signal to sense a voltage or a current for every position of the sensor array or a change in the resistance. For example, when the reduction in a resistance in a node of an arbitrary position is sensed, the first controller 1200 senses that the conductive fiber is stretched in the corresponding position.

The first controller 1200 senses the change in the resistance for every node included in the sensor array to determine whether to be contracted/stretched at each node.

The display unit 2000 includes a light emitting diode array 2100 and a second controller 2200. For example, the light emitting diode array 2100 is an LED or an OLED, but is not specifically limited to a type of light emitting diode.

The second controller 2200 transmits a control signal to the light emitting diode array 2100 to control a state (on/off or a brightness) of light emitting diodes according to an arrangement position of the light emitting diode or according to a contracted/stretched situation of the conductive fiber.

In the present disclosure, the first controller 1200 senses a resistance change of each node (the resistance change corresponds to a contracted/stretched situation at every node) which is sensed through the sensor array, through an electrical signal acquired for every position of the node and transmits a contracting/stretching signal for every node for controlling a light emitting diode according to a resistance change for every node to the second controller 2200. The second controller 2200 receives the contracting/stretching signal and transmits a control signal for controlling a light emitting diode to the light emitting diode array 2100 according to a predetermined criteria.

Figure 12:
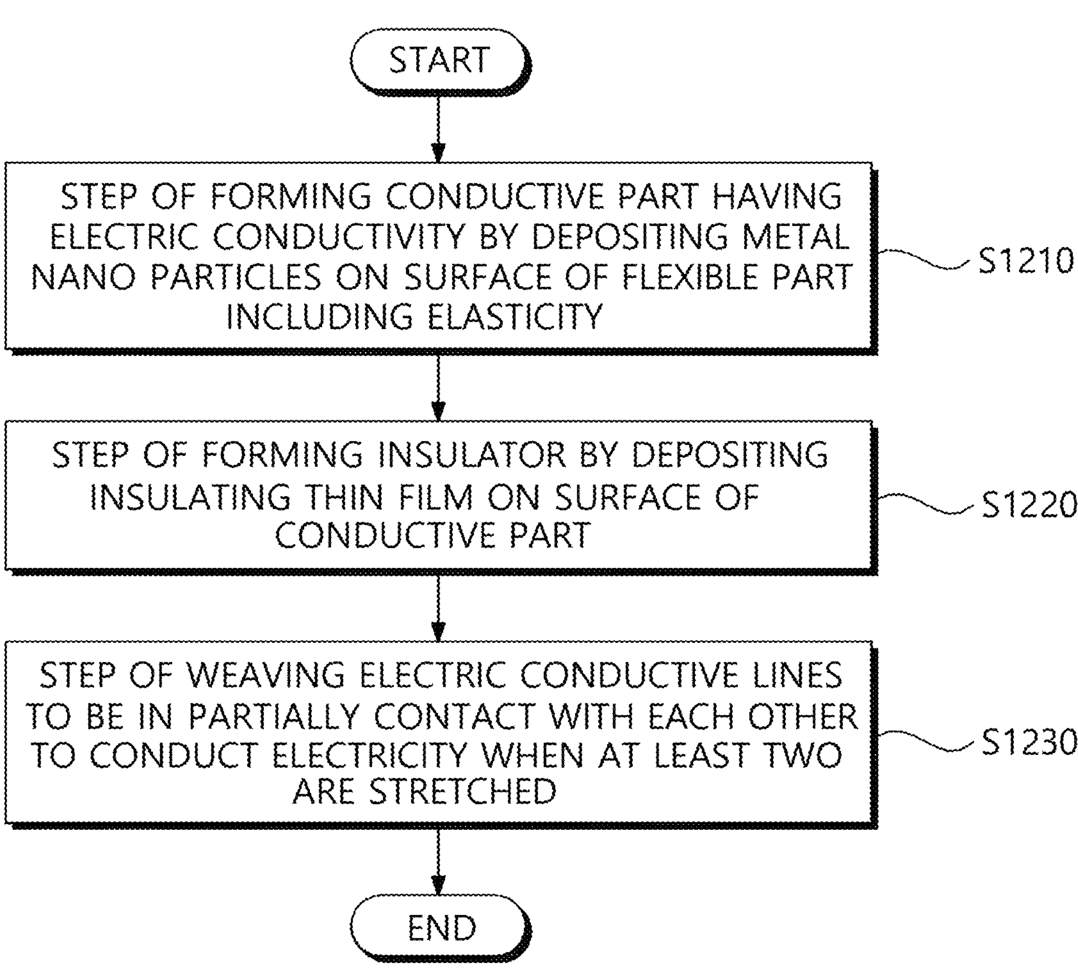
FIG. 12 is a flowchart illustrating a manufacturing method of a fiber-based strain sensor according to an exemplary embodiment of the present disclosure.

FIG. 12 is a flowchart illustrating a manufacturing method of a fiber-based strain sensor according to an exemplary embodiment of the present disclosure. The manufacturing method of a fiber-based strain sensor is performed to manufacture a fiber-based strain sensor and a repeated description with the fiber-based strain sensor in the above-described drawings will be omitted.

The manufacturing method of a fiber-based strain sensor includes: a step S1210 of forming a conductive part having an electric conductivity by depositing metal nano particles in a flexible part including elasticity, a step S1220 of forming an insulator by depositing an insulating thin film on a surface of the conductive part, and a step S1230 of weaving at least two electric conductive lines to be in partially contact with each other when the electric conductive lines are stretched, to conduct electricity.

In the step 1220 of forming an insulator by depositing an insulating thin film on a surface of the conductive part, the insulator is formed by selective irradiation of ultraviolet ray or laser or selective heat treatment.

In the step S1220 of forming an insulator by depositing an insulating thin film on a surface of the conductive part, the insulator is deposited into the flexible part on which the conductive part is deposited to generate an electric conductive line.

In the step S1230 of weaving at least two electric conductive lines to be in partially contact with each other when the electric conductive lines are stretched, to conduct electricity, the electric conductive line generated in the step S1210 and the electric conductive line generated in the step S1220 are woven to be twisted or two or more of electric conductive lines generated in the step S1220 are twisted with each other.

In FIG. 12, the respective processes are sequentially performed, but this is merely illustrative and those skilled in the art may apply various modifications and changes by changing the order illustrated in FIG. 12 or performing one or more processes in parallel or adding another process without departing from the essential gist of the exemplary embodiment of the present disclosure.

Accordingly, the electric conductive line 10 of the present disclosure includes a flexible part 100, a conductive part 200, and an insulator 300.

The electric conductive line 10 includes a flexible part 100 implemented with an elastic fiber, a conductive part 200 which represents a conductive fiber formed of metal nano particles formed in the elastic fiber, and an insulator 300 which represents an elastic fiber including an insulating thin film formed on a surface of the conductive fiber. At this time, the surface is implemented as an insulating layer and the insider is implemented as a conductive layer.

The fiber-based strain sensor 1 is implemented as a fiber-based sensor in which two or more insulating layer/conductive layer elastic fibers are twisted to form resistance therebetween or implemented as a fiber-based sensor in which one or more insulating layer/conductive layer elastic fibers and one or more elastic fiber only formed with a conductive layer are twisted to form resistance therebetween.

The mutual resistance forms a resistance as low as a conductor only upon stretching and forms a resistance as high as an insulator when it is not stretched to have a negative strain gauge value.

The elastic fiber uses a fiber formed of a polymer material and includes any one selected from a group consisting of polyurethane, styrene-butadiene-styrene (SBS), styrene butadiene rubber (SBR), and polydimethylsiloxane (PDMS), but is not necessarily limited thereto.

The conductive layer includes various metal materials such as silver nano particles, gold nano particles, copper nano particles, and platinum nano particles, a conductive organic material such as PEDOT:PSS, or nano materials such as nano wires, but is not necessarily limited thereto.

The insulating layer is an organic layer having an insulator characteristic, such as SU-8, polyimide, PVA, PMMA, or CYTOP or oxide such as SiOx or HfOx, but is not necessarily limited thereto.

According to the exemplary embodiment of the present disclosure, the insulating layer includes a thin film which adjusts a degree of causing crack according to the strain by adjusting a modulus to be different through selective curing such as UV.

Further, a thin film which adjusts a degree of causing crack according to the strain by adjusting a thickness and a hardness of the insulating layer is included.

The fiber-based strain sensor 1 may adjust a degree of resistance change according to a number of times of twisting the electric conductive line 10 or a degree of twisting the electric conductive line.

The electric conductive line 10 may be used not only for a combination of fibers, but also for a combination of an elastic substrate having an insulating layer/conductive layer and fiber, and a combination of substrates.

Further, the electric conductive line is also applied to various applications (a monitoring device or a wearable display) which uses the electric conductive line 10 as a part of a wiring line) to be used.

The operation according to the exemplary embodiment of the present disclosure may be implemented as a program instruction which may be executed by various computers to be recorded in a computer readable medium. The computer readable medium indicates an arbitrary medium which participates to provide a command to a processor for execution. The computer readable medium may include solely a program command, a data file, and a data structure or a combination thereof. For example, the computer readable medium may include a magnetic medium, an optical recording medium, and a memory. The computer program may be distributed on a networked computer system so that the computer readable code may be stored and executed in a distributed manner. Functional programs, codes, and code segments for implementing the present embodiment may be easily inferred by programmers in the art to which this embodiment belongs.

The above description illustrates a technical spirit of the present invention as an example and various changes, modifications, and substitutions become apparent to those skilled in the art within a scope of an essential characteristic of the present invention. Therefore, as is evident from the foregoing description, the exemplary embodiments and accompanying drawings disclosed in the present invention do not limit the technical spirit of the present invention and the scope of the technical spirit is not limited by the exemplary embodiments and accompanying drawings. The protection scope of the present invention should be interpreted based on the following appended claims and it should be appreciated that all technical spirits included within a range equivalent thereto are included in the scope of the present invention.

What is claimed is:

1. A fiber-based strain sensor comprising:

at least one first electric conductive line including a first flexible part having electric conductivity; and at least one second electric conductive line which is woven to be in partial contact with the at least one first electric conductive line, including a second flexible part having electric conductivity, and being implemented to conduct electricity with the first flexible part having electric conductivity in a stretched state, wherein the at least one first electric conductive line and the at least one second electric conductive line form a physical structure comprising: a conductive part having electric conductivity formed by depositing metal nano particles inside the first flexible part and the second flexible part; and an insulator formed by depositing an insulating thin film on a surface of the conductive part, wherein the at least one first electric conductive line and the at least one second electric conductive line are implemented with a negative gauge factor (N-GF) configured such that current flows as the at least one first electric conductive line and the at least one second electric conductive line directly contact each other through a crack formed by the insulator only in the stretched state, and wherein a degree of causing a crack according to strain is adjusted by the insulating thin film having a preset modulus, thickness, or hardness through a curing process by selective irradiation of ultraviolet curing (UV-curing).

2. The fiber-based strain sensor according to claim 1, wherein the at least one first electric conductive line and the at least one second electric conductive line are woven to be twisted and a first node connected to the at least one first electric conductive line and a second node connected to the at least one second electric conductive line forms a mutual resistance which is formed to be equal to or lower than a predetermined resistance according to a stretched state.

3. The fiber-based strain sensor according to claim 2, wherein a degree of resistance change is adjusted by adjusting a number of times of twisting the at least one first electric conductive line and the at least one second electric conductive line or a degree of twisting the at least one first electric conductive line and the at least one second electric conductive line.

4. The fiber-based strain sensor according to claim 2, wherein the first flexible part and the second flexible part include at least one of polyurethane, styrene-butadiene-styrene (SBS), styrene butadiene rubber (SBR), and polydimethylsiloxane (PDMS) which are formed of polymer materials and the conductive part includes at least one of metal material implemented by nano particles, a conductive organic material, and nano materials.

5. The fiber-based strain sensor according to claim 2, wherein the insulator includes at least one of organic materials which form an insulator characteristic, such as SU-8, polyimide, PVA, PMMA, or CYTOP or oxide, such as SiOx or HfOx.

6. The fiber-based strain sensor according to claim 2, wherein the insulator adjusts a degree of causing a crack according to strain, by adjusting a modulus, a thickness, or a hardness by means of curing.

7. The fiber-based strain sensor according to claim 1, wherein the fiber-based strain sensor is implemented to be applied to a stretchable device and the stretchable device is applied in a position in which the fiber-based strain sensor is stretchable in a length direction.

8. A monitoring system, comprising:

a fiber-based strain sensor including: at least one first electric conductive line including a first flexible part having electric conductivity and at least one second electric conductive line which is woven to be in partial contact with the at least one first electric conductive line, including a second flexible part having electric conductivity, and being implemented to conduct electricity with the first flexible part having electric conductivity in a stretched state;

a stretchable device to which the fiber-based strain sensor is applied and which is implemented to be stretchable by a motion; and a monitoring device which receives current generated upon stretching in a wired or wireless method to monitor the state of the stretchable device, wherein the at least one first electric conductive line and the at least one second electric conductive line form a physical structure comprising: a conductive part having electric conductivity formed by depositing metal nano particles inside the first flexible part and the second flexible part; and an insulator formed by depositing an insulating thin film on a surface of the conductive part, wherein the at least one first electric conductive line and the at least one second electric conductive line are implemented with a negative gauge factor (N-GF) configured such that current flows as the at least one first electric conductive line and the at least one second electric conductive line directly contact each other through a crack formed by the insulator only in the stretched state, and wherein a degree of causing a crack according to strain is adjusted by the insulating thin film having a preset modulus, thickness, or hardness through a curing process by selective irradiation of ultraviolet curing (UV-curing).

9. The monitoring system according to claim 8, wherein the stretchable device is implemented to apply the fiber-based strain sensor in a position to be stretchable in a length direction so that the at least one first electric conductive line and the at least one second electric conductive line conduct electricity upon stretching and when the electricity is conducted by the stretching, the monitoring device predicts a shape of the stretchable device to provide a feedback in real time.

* * * * *